United States Patent [19]

Colignon et al.

[11] Patent Number: 5,384,422
[45] Date of Patent: Jan. 24, 1995

[54] PROCESS FOR THE PRODUCTION OF LIGHT-COLORED α-SULFOFATTY ACID ALKYL ESTER ALKALI METAL SALT PASTES

[75] Inventors: Dietmar Colignon, Erkrath; Erich Dorra, Duesseldorf; Guenter Panthel, Haan; Wolfgang Schmidt, Monheim; Norbert Wrede, Duesseldorf, all of Germany

[73] Assignee: Henkel Kommanditgesellschaft auf Aktien, Duesseldorf, Germany

[21] Appl. No.: 952,714

[22] PCT Filed: May 21, 1991

[86] PCT No.: PCT/EP91/00951
§ 371 Date: Nov. 25, 1992
§ 102(e) Date: Nov. 25, 1992

[87] PCT Pub. No.: WO91/18874
PCT Pub. Date: Dec. 12, 1991

[30] Foreign Application Priority Data

May 30, 1990 [DE] Germany ............................ 4017467

[51] Int. Cl.6 ............................................. C07C 303/32
[52] U.S. Cl. ......................................... 554/98; 544/85; 544/96; 544/97
[58] Field of Search ........................ 554/97, 98, 85, 96

[56] References Cited

U.S. PATENT DOCUMENTS 3,251,868  6/1966  Steen et al. ................... 260/40 C
4,547,318  10/1985  Kloetzer et al. .............. 260/40 C

FOREIGN PATENT DOCUMENTS 401925   5/1920  Austria ................................. 554/97
0222237  5/1987  European Pat. Off. .
3319591  5/1983  Germany .

*Primary Examiner*—José G. Dees
*Assistant Examiner*—Deborah D. Carr
*Attorney, Agent, or Firm*—Wayne C. Jaeschke; John E. Drach; Henry E. Millson, Jr.

[57] ABSTRACT

In the production of α-sulfofatty acid alkyl ester alkali metal salt pastes by reaction of fatty acid alkyl esters with gaseous $SO_3$, subsequent after-reaction in liquid phase and neutralization with aqueous alkali metal hydroxide solutions, the crude sulfonation product is fed to an at least two-stage cascade of stirred tanks equipped with heating and cooling systems in which it is subjected with mechanical agitation to a temperature-controlled after-reaction until a degree of sulfonation of at least 90% is reached, after which the aged sulfonation product is further processed in known manner to α-sulfofatty acid alkyl ester alkali metal salt pastes.

16 Claims, No Drawings

PROCESS FOR THE PRODUCTION OF LIGHT-COLORED α-SULFOFATTY ACID ALKYL ESTER ALKALI METAL SALT PASTES

BACKGROUND OF THE INVENTION

1. Field of the Invention

This invention relates to a process for the production of light-colored α-sulfofatty acid alkyl ester alkali metal salt pastes, in which the crude sulfonation product is subjected immediately after the sulfonation reaction to a temperature-controlled after-reaction in a substantially ideally mixed liquid phase until a degree of sulfonation of at least 90% is reached.

2. Statement of Related Art

α-Sulfofatty acid alkyl ester alkali metal salts are acquiring increasing significance as surfactants for detergents and cleaning preparations based on renewable natural raw materials. In known processes, the α-sulfofatty acid alkyl ester alkali metal salts are obtained in the form of aqueous solutions or pastes by neutralization of α-sulfofatty acid alkyl esters which may be synthesized by reaction of lower fatty acid alkyl esters with gaseous $SO_3$. In the final analysis, the basis for the production of the α-sulfofatty acid alkyl ester alkali metal salts are fats and oils of natural origin from which the lower fatty acid alkyl esters are obtained by lipolysis and subsequent esterification of the free fatty acids with lower alkanols or by transesterification of the natural triglycerides with lower alkanols. In both reactions, methanol is preferably used as the lower alkanol. The lower fatty acid alkyl esters are mixtures in which $C_{6-22}$ fatty acid residues occur, the chain length distribution being dependent on the origin of the natural fats or oils. In many cases, these fatty acid ester mixtures are not used for the synthesis as such, but rather in the form of certain fractions. Sulfonation of the fatty acid ester mixtures with gaseous $SO_3$ gives acidic α-sulfofatty acid alkyl esters which are converted into aqueous pastes of α-sulfofatty acid alkyl ester alkali metal salts by neutralization to a pH value of 6 to 8. The crude α-sulfofatty acid alkyl esters and their alkali metal salts are more or less colored products which generally have to be treated with typical bleaches before and/or after neutralization.

The sulfonation of the fatty acid alkyl esters is normally carried out with gaseous $SO_3$ at temperatures in the range from 30° to 100° C., the molar ratio of fatty acid ester to $SO_3$ being from 1:1.2 to 1:1.8. The reaction of the fatty acid alkyl esters with $SO_3$ takes place in two steps. In a first, rapid step, 2 molecules $SO_3$ react with 1 molecule fatty acid alkyl ester to form a mixed anhydride of α-sulfofatty acid and alkyl sulfuric acid. In a slow, second step, the mixed anhydride acts as sulfonating agent for unreacted fatty acid alkyl ester. The first step takes place in the particular typical sulfonation reactor used, for example in a falling-film reactor or in a sulfonation cascade. Very little information is available to show how the second reaction step is carried out in known processes, generally being confined to the reaction temperature and, at most, to the reaction time. Thus, according to DE-OS 31 23 681, the sulfonation product is said to be aged at 30° to 100° C. According to DE-OS 33 34 517, the sulfonation product is aged for 10 to 20 minutes at 80° to 100° C.

During the work culminating in the present invention, it was found that the conduct of the second step of the sulfonation reaction is crucially important to the degree of sulfonation and to the quality of the end product. It has been found that product quality depends to a large extent on exact temperature control and on a narrow holding time distribution in the after-reaction. Short holding times lead to readily bleachable, but inadequately sulfonated α-sulfofatty acid alkyl ester alkali metal salt pastes. Long holding times lead to high degrees of sulfonation, but also to strongly colored products which cannot be bleached to the necessary color values after neutralization.

Known holding-time installations are unable to satisfy the dual requirement of a narrow holding time distribution and exact temperature control. Standard reactors operated solely with a heating and cooling circuit lead to far too broad a holding time spectrum on account of the constant back-mixing. Following temperature-controlled pipe coils always have to operated under full turbulent flow conditions, i.e. under plug-flow conditions, and accordingly cannot be operated independently of the output of the sulfonation reactor.

Accordingly, the problem addressed by the present invention was to provide a process which would enable the crude sulfonation product in the production of light-colored α-sulfofatty acid alkyl ester alkali metal salts by reaction of fatty acid alkyl esters with gaseous $SO_3$ and neutralization with aqueous alkali metal hydroxide solutions to be subjected to an after-reaction under exact temperature control and, at the same time, a narrow holding time distribution before it was neutralized and bleached in known manner.

DESCRIPTION OF THE INVENTION

It has been found that a conventional cascade of stirred tanks following the sulfonation reactor and equipped with heating and cooling systems ideally satisfies the conditions which the second reaction step of the fatty acid alkyl ester sulfonation requires in regard to temperature control and holding time behavior. The cascade may consist of any number of stirred tanks arranged one behind the other and preferably consists of four stirred tanks. If the cascade of stirred tanks consists of four or more units, its holding time behavior is equivalent to that of a turbulent-flow tube. The average holding time for the second sulfonation step may readily be adjusted through the liquid level in the individual stirred tanks. By means of several ideally mixed stirred tanks arranged one behind the other, it is possible to establish both isothermal reaction conditions and also any other desired temperature profile.

The present invention relates to a process for the production of light-colored α-sulfofatty acid alkyl ester alkali metal salt pastes by reaction of fatty acid alkyl esters with gaseous $SO_3$, subsequent after-reaction in a substantially ideally mixed liquid phase and neutralization with aqueous alkali metal hydroxide solutions, characterized in that a) fatty acid alkyl esters are reacted with an at least 10% molar excess of $SO_3$ in a typical sulfonation reactor, b) the crude sulfonation product is fed to an at least two-stage cascade of stirred tanks with heating and cooling systems in which it is subjected with mechanical agitation to a temperature-controlled after-reaction until a degree of sulfonation of at least 90% is reached and c) the sulfonation product aged in this way is further processed in known manner to α-sulfofatty acid alkyl ester alkali metal salt pastes.

The fatty acid esters are reacted with gaseous $SO_3$ as the sulfonation reagent at temperatures in the range from 30° to 100° C. The $SO_3$ is reacted with the fatty acid esters after dilution with air or nitrogen, preferably in the form of a gas mixture containing 1 to 10% by volume $SO_3$. The quantity in which the $SO_3$ is used is preferably gauged in such a way that the molar ratio of fatty acid ester to $SO_3$ is from 1:1.2 to 1:1.8. This reaction may be carried out in typical reactors suitable for the sulfonation of organic compounds, such as fatty alcohols, alkyl benzenes or olefins, more particularly in falling-film reactors or multistage cascades of stirred tanks.

The temperature-controlled after-reaction is carried out in a conventional cascade of stirred tanks equipped with heating and cooling systems. The cascade may comprise from 3 to 6 stirred tanks, four-stage cascades being preferred. The heating and cooling systems of the cascade of stirred tanks preferably consist of pipe coils or heat-transfer jackets.

During the after-reaction, the exothermically reacting reaction mixture is kept at temperatures of 60° to 100° C. in all the stirred tanks of the cascade, temperatures in the range from 80° to 90° C. being preferred.

During the temperature-controlled after-reaction, the sulfonation product should be present in substantially ideally mixed liquid phase. The mechanical agitation of the sulfonation product required for this purpose in the cascade of stirred tanks is obtained by stirring, by introduction of the product under pressure or by installed chicane-like baffles.

The crude sulfonation product is left in the cascade of stirred tanks until a degree of sulfonation of at least 90% and preferably 94 to 98% is reached. To this end, the crude sulfonation product is left in the cascade of stirred tanks for 10 to 60 minutes and preferably for 20 to 40 minutes.

In the production of light-colored α-sulfofatty acid alkyl ester alkali metal salt pastes in accordance with the invention, the aged sulfonation product is neutralized and bleached in known manner after the temperature-controlled after-reaction.

The aged sulfonation product is neutralized with aqueous alkali metal hydroxide solutions, preferably with aqueous sodium hydroxide solutions.

The crude sulfonation products and their alkali metal salts are more or less colored substances. For this reason, they have to be bleached by known methods before and/or after neutralization, aqueous hydrogen peroxide and/or hypochlorite solutions preferably being used as bleaches. Bleaching before neutralization with hydrogen peroxide is described in DE-PS 11 79 931. According to DE-AS 12 34 709, the acidic α-sulfofatty acid alkyl ester is treated with aqueous hydrogen peroxide solution in a first bleaching step. The partly bleached sulfonation product is then neutralized before being treated with more hydrogen peroxide solution or aqueous hypochlorite solution in a second bleaching step. According to DE-OS 33 19 591, the partly neutralized sulfonation product is initially bleached with aqueous hypochlorite solution at pH values of 7 to 11. Aqueous hydrogen peroxide solution is then added at pH values of $\leq 7$ to stabilize the color values reached.

In the context of the invention, fatty acid alkyl esters are understood to be lower alkyl esters of saturated fatty acids, more particularly esters of fatty acids containing 10 to 18 carbon atoms and saturated aliphatic alcohols containing 1 to 4 carbon atoms. Basically, individual fatty acid alkyl esters may be used as starting material. In general, however, ester mixtures of the type obtainable from fats and oils of natural origin either by ester cleavage and subsequent esterification with lower alkanols or by transesterification with lower alkanols by known methods are used as the starting material, the corresponding fatty acid methyl ester mixtures being preferred. If the fatty acid ester mixtures obtained in this way have relatively large percentage contents of esters of fatty acids containing less than 10 carbon atoms, these "head-fractionated fatty acid esters" are generally removed by distillation. Apart from the $CH_2$ group in the α-position to the ester group, the fatty acid esters should not contain any sulfatable or sulfonatable groups. For this reason, hydroxyfatty acid esters or mixtures containing hydroxy-fatty acid esters are not suitable as starting materials. Fatty acid ester mixtures containing non-negligible quantities of esters of unsaturated fatty acids, more particularly esters having an iodine value above 5, are only suitable as starting materials after saturation of the double bonds in the course of hardening by hydrogenation using known methods. During the hydrogenation, the iodine values of the ester mixtures are preferably reduced to values of 0.2 and lower.

EXAMPLES

Examples 1 to 6

The starting material used was a technical palmitic/stearic acid methyl ester (in % by weight according to chain length in the fatty acid part: 0.2 $C_{12}$; 1.2 $C_{14}$; 61.4 $C_{16}$; 0.9 $C_{17}$; 35.9 $C_{18}$; 0.4 $C_{20}$; average molecular weight 281.5; acid value 1.1; iodine value 0.1; saponification value 202.1). The fatty acid methyl ester was continuously sulfonated with an $SO_3$/air mixture (5% by volume $SO_3$) in a molar ratio of 1:1.25 in a standard falling-film reactor at a temperature of 80° C. Individual batches of the resulting reaction mixture were subjected to the after-reaction in a holding-time cascade of four stirred tanks with holding times of 10, 30 and 60 minutes at 80° and 90° C.

Following the after-reaction, the aged batches were neutralized with aqueous sodium hydroxide solution. Aqueous hydrogen peroxide solution was introduced into the reaction mixture with the neutralization base, hydrogen peroxide being added in a quantity of 1.5% by weight, expressed as 100% substance and based on WAS. After neutralization, all the batches were stirred for 20 hours at a temperature of 80° C. The Klett color values were then measured on solutions containing 5% by weight washing-active substance at pH 7.5 in a 5 cm cuvette using a blue filter (420 nm).

The after-reaction temperature and the holding time and also the degree of sulfonation reached and the associated Klett color value are shown for each Example in the following Table.

TABLE

Degree of sulfonation and Klett color value in dependence upon the after-reaction temperature and holding time

| Example | Temperature (°C.) | Holding time (mins.) | Degree of sulfonation (%) | Klett color value |
|---|---|---|---|---|
| 1 | 80 | 10 | 90 | 100 |
| 2 | 80 | 30 | 94 | 200 |

TABLE-continued

Degree of sulfonation and Klett color value in dependence upon the after-reaction temperature and holding time

| Example | Temperature (°C.) | Holding time (mins.) | Degree of sulfonation (%) | Klett color value |
|---|---|---|---|---|
| 3 | 80 | 60 | 97 | 250 |
| 4 | 90 | 10 | 92 | 150 |
| 5 | 90 | 30 | 96 | 200 |
| 6 | 90 | 60 | 97 | 400 |

What is claimed is:

1. A process for the production of a light colored paste of an α-sulfofatty acid alkyl ester alkali metal salt which comprises:
   (1) contacting a fatty acid alkyl ester that does not contain sulfatable or sulfonatable groups other than the α-$CH_2$ group with gaseous sulfur trioxide, wherein the sulfur trioxide is present in at least a 10% molar excess, to form a crude sulfonation product;
   (2) passing said crude sulfonation product through a post-reaction zone until a degree of sulfonation of at least 90% is reached, wherein said post-reaction zone is comprised of a cascade comprised of at least two tank reactors each of which is maintained at a temperature of from about 60° C. to about 100° C., and wherein the crude sulfonation product is mechanically agitated in the tanks, and the crude sulfonation product has a residence time in the post-reaction zone of from about 10 to about 60 minutes; and
   (3) bleaching and neutralizing the product of step (2) to form a light colored paste of an α-sulfofatty acid alkyl ester alkali metal salt.

2. The process of claim 1 wherein in step (1) the sulfur trioxide is part of a mixture comprised of up to 10% by volume sulfur trioxide and the remainder air or up to 10% by volume sulfur trioxide and the remainder nitrogen.

3. The process of claim 1 wherein said post-reaction zone is comprised of a cascade of from 3 to 6 tank reactors.

4. The process of claim 3 wherein said cascade is comprised of 4 tank reactors.

5. The process of claim 1 wherein in step (2) the heating and cooling systems of said reactors are comprised of pipe coils or heat transfer jackets.

6. The process of claim 1 wherein the mechanical agitation in said tank reactors is achieved through stirring, chicane-like baffles, or by introduction of said crude sulfonation product under pressure.

7. The process of claim 1 wherein in step (2) said degree of sulfonation is from about 94% to about 98%.

8. The process of claim 1 wherein in step (3) bleaching is carried out with hydrogen peroxide or hypochlorite.

9. The process of claim 1 wherein said fatty acid alkyl ester is a methyl ester.

10. The process of claim 9 wherein said fatty acid alkyl ester is a mixture of fatty acid methyl esters obtained by transesterification of natural fats or oils with methanol.

11. The process of claim 1 wherein in step (2) said temperature is in the range of from about 80° to about 90° C.

12. The process of claim 1 wherein in step (2) the residence time in the post-reaction zone is from about 20 to about 40 minutes.

13. The process of claim 1 wherein in step (1) the fatty acid alkyl ester is an ester of a fatty acid containing 10 to 18 carbon atoms and a saturated aliphatic alcohol containing 1 to 4 carbon atoms.

14. The process of claim 1 wherein in step (1) the fatty acid alkyl ester is an ester of a fatty acid containing 10 to 18 carbon atoms and a saturated aliphatic alcohol containing 1 to 4 carbon atoms; in step (2) said temperature is in the range of from about 80° to about 90° C. and the residence time in the post-reaction zone is from about 20 to about 40 minutes, and wherein the post-reaction zone is comprised of a cascade of from 3 to 6 tank reactors.

15. The process of claim 14 wherein in step (2) said degree of sulfonation is from about 94% to about 98%, and said cascade is comprised of 4 stirred tank reactors.

16. The process of claim 14 wherein said fatty acid alkyl ester is a mixture of fatty acid methyl esters obtained by transesterification of natural fats or oils with methanol.

* * * * *